US012648690B2

(12) United States Patent
Wei et al.

(10) Patent No.: US 12,648,690 B2
(45) Date of Patent: Jun. 9, 2026

(54) SYSTEMS AND METHODS FOR PHASE-STABILIZED COMPLEX DECORRELATION ANGIOGRAPHY

(71) Applicant: OREGON HEALTH & SCIENCE UNIVERSITY, Portland, OR (US)

(72) Inventors: Xiang Wei, Portland, OR (US); Yali Jia, Portland, OR (US)

(73) Assignee: OREGON HEALTH & SCIENCE UNIVERSITY, Portland, OR (US)

( * ) Notice: Subject to any disclaimer, the term of this patent is extended or adjusted under 35 U.S.C. 154(b) by 348 days.

(21) Appl. No.: 18/273,969

(22) PCT Filed: Feb. 1, 2022

(86) PCT No.: PCT/US2022/014647
§ 371 (c)(1),
(2) Date: Jul. 24, 2023

(87) PCT Pub. No.: WO2022/169722
PCT Pub. Date: Aug. 11, 2022

(65) Prior Publication Data
US 2024/0407643 A1      Dec. 12, 2024

Related U.S. Application Data

(60) Provisional application No. 63/144,666, filed on Feb. 2, 2021.

(51) Int. Cl.
*A61B 3/10*          (2006.01)
*A61B 3/12*          (2006.01)

(52) U.S. Cl.
CPC ............ *A61B 3/102* (2013.01); *A61B 3/1233* (2013.01)

(58) Field of Classification Search
CPC ..... A61B 3/102; A61B 3/1233; A61B 5/7207; A61B 5/7246; A61B 2576/00; A61B 5/0066
USPC ........................................................ 351/206
See application file for complete search history.

(56) References Cited

U.S. PATENT DOCUMENTS

| | | | |
|---|---|---|---|
| 2015/0157205 A1* | 6/2015 | Buckland | A61B 3/0025 351/246 |
| 2016/0206195 A1* | 7/2016 | Huang | A61B 3/1233 |
| 2016/0317020 A1 | 11/2016 | Liu et al. | |
| 2017/0319060 A1 | 11/2017 | Huang et al. | |
| 2018/0055355 A1* | 3/2018 | Sarunic | A61B 3/1241 |
| 2018/0182082 A1 | 6/2018 | Jia et al. | |
| 2018/0317851 A1 | 11/2018 | Jia et al. | |
| 2018/0353064 A1* | 12/2018 | Soetikno | A61K 49/0071 |
| 2019/0150729 A1 | 5/2019 | Huang et al. | |

(Continued)

*Primary Examiner* — Mohammed A Hasan

(74) *Attorney, Agent, or Firm* — Schwabe, Williamson & Wyatt, P.C.

(57) ABSTRACT

Disclosed are methods and systems for phase-stabilized complex decorrelation (PSCD) optical coherence tomography (OCT) angiography (OCTA). In embodiments, a PSCD OCTA method includes performing phase stabilization on a complex-valued OCT data set to generate a phase-stabilized OCT dataset. The method further includes performing a complex decorrelation on the phase-stabilized OCT dataset to generate an OCTA dataset. One or more OCTA images may be generated based on the OCTA dataset. Other embodiments may be described and claimed.

20 Claims, 11 Drawing Sheets

(56) References Cited

U.S. PATENT DOCUMENTS

2021/0145277 A1*   5/2021   Wei ............................ G06T 5/50
2021/0196120 A1*   7/2021   Puyo .................... A61B 3/0025

* cited by examiner

PSCD  vs.  OMAG

1100

SYSTEMS AND METHODS FOR PHASE-STABILIZED COMPLEX DECORRELATION ANGIOGRAPHY

CROSS-REFERENCE TO RELATED APPLICATIONS

This application is a 371 U.S. national stage application of PCT/US2022/014647, filed on Feb. 1, 2022, which claims priority to U.S. Provisional Patent Application No. 63/144, 666, filed Feb. 2, 2021. Each of these applications is incorporated by reference in its entirety.

ACKNOWLEDGEMENT OF GOVERNMENT SUPPORT

This invention was made with government support under R01 EY024544 and R01 EY027833 awarded by The National Institutes of Health. The government has certain rights in the invention.

FIELD

Generally, the field involves imaging using optical coherence tomography. In particular, the field involves imaging using phase-stabilized complex decorrelation angiography.

BACKGROUND

Optical coherence tomography (OCT) angiography (OCTA) is a recently developed vascular imaging method used in many experimental and clinical applications. As a non-invasive method, OCTA can provide high-sensitivity, high-resolution, three-dimensional angiograms with minimal side effects. OCTA is generated by measuring motion contrast in the reflectance signal encoded in the raw spectrum data acquired by the OCT system. This reflectance signal is complex, containing both amplitude and phase components. Depending on which signal is processed, OCTA systems can be described as either amplitude-, phase-, or (in the case where both signals are processed to form the image) complex-based. The choice of signal to process is not immaterial, as it determines flow signal sensitivity, dynamic range, and dependency on scan quality.

Each signal offers some advantages and disadvantages. The phase signal is the most sensitive, being capable of detecting only slight variation between in the reflectance signal, and in certain circumstances it can also recover flow velocity. However, the extreme sensitivity of the phase signal also means that it is vulnerable to system phase and bulk motion noise, so phase-based OCTA processing requires phase stabilization approaches. Amplitude-based OCTA loses this extreme sensitivity to motion, but can consequently forego phase stabilization and bulk motion correction. Loss of sensitivity may seem problematic, but this loss is rarely material since amplitude-based approaches have sufficient sensitivity to detect blood flow in capillaries, which is the minimum sensitivity required from a clinical or anatomic perspective. Finally, complex-based OCTA has the theoretical advantage of utilizing all of the information available in the reflectance signal. However, like phase-based methods, phase compensation is a critical requirement.

BRIEF DESCRIPTION OF THE SEVERAL VIEWS OF THE DRAWINGS

FIG. 3A is a flow phantom phase variance image without phase stabilization; FIG. 3B is a 12-mm wide-field OCT phase variance image without phase stabilization; FIG. 3C is a flow phantom phase variance image with phase stabilization; and FIG. 3D is a 12-mm-wide-field OCT phase variance image with phase stabilization. The average phase variance value along the axial direction is plotted under each image. With phase stabilization, the phase variance values in FIGS. 3C and 3D are consistently near to zeros, indicating a good performance of phase correction.

FIG. 4A illustrates plots of normalized OCTA values, where $T_h$ is the high threshold, and $T_l$ is the low threshold. The shaded areas indicate the dynamic range of the different methods. The circles in FIGS. 4C, 4D, and 4E indicate the signals used for calculating dynamic range. FIG. 4B illustrates the flow phantom's OCT structure image.

FIGS. 7B, 7C, 7D illustrate en face OCTA images at 100% of signal strength, while FIGS. 7E, 7F, and 7G illustrate en face OCTA images at 10% of signal strength.

FIG. 8A is a 12×23 mm wide-field PSCD OCTA image. FIGS. 8B-8E are zoomed localized images cropped from FIG. 8A.

DETAILED DESCRIPTION

Figure 1:
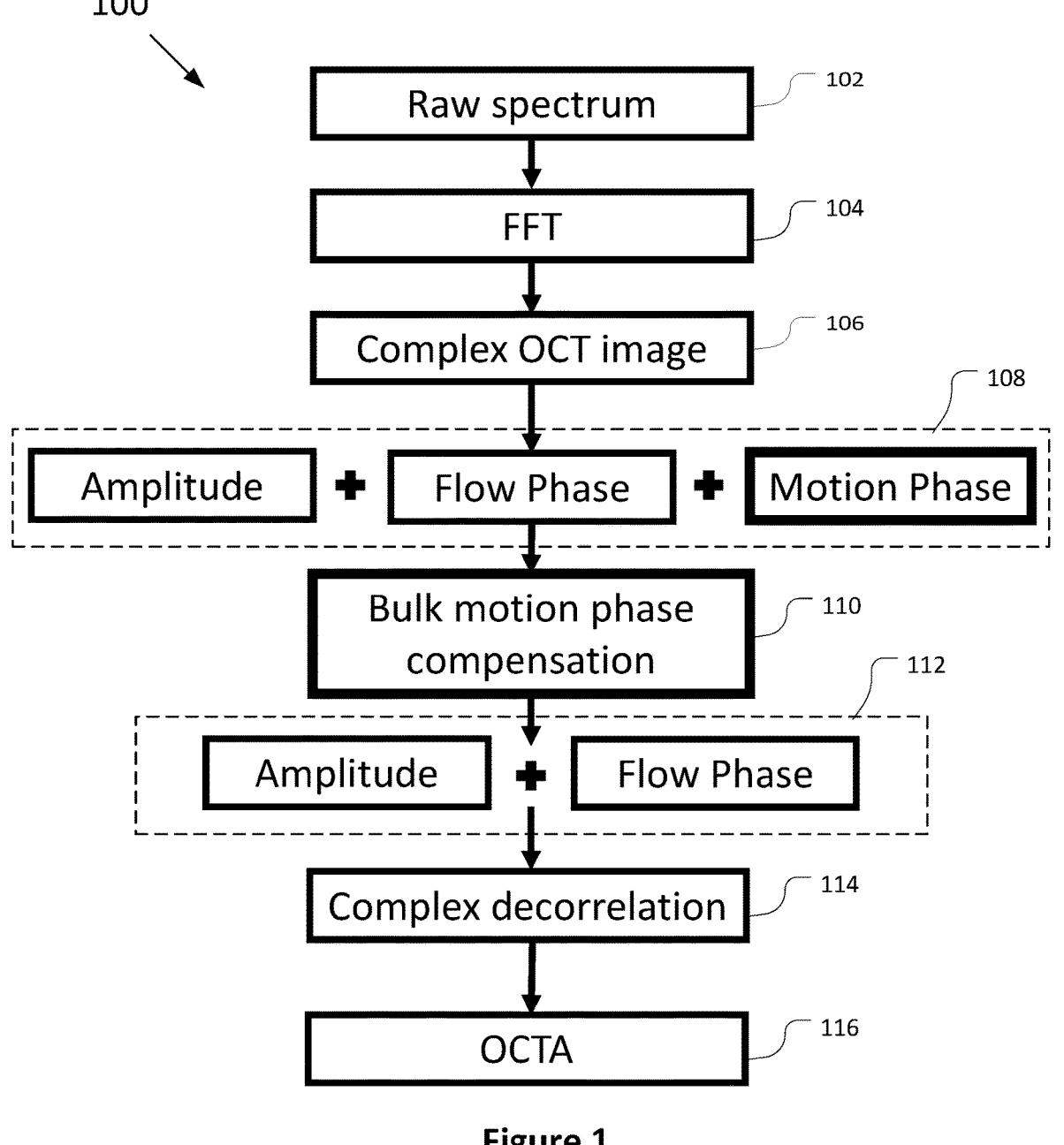
FIG. 1 is a flowchart of a phase stabilized complex decorrelation (PSCD) OCT process, in accordance with various embodiments.

Disclosed are methods and systems for phase-stabilized complex decorrelation (PSCD) optical coherence tomography (OCT) angiography (OCTA) to generate OCTA images. The method has been validated using three different types of OCT systems and compared with conventional complex- and amplitude-based OCTA algorithms, as discussed further below. The results indicate that the PSCD method can more accurately remove bulk motion induced artifacts, and is less dependent on OCT reflectance than conventional complex methods.

The disclosed systems and methods are applicable to complex-valued signals, such as OCT signals having both amplitude and phase information. In some embodiments, the disclosed methods and systems are applicable to phase-based functional OCT imaging applications. Examples of functional OCT imaging include retinal Doppler OCT, OCTA, and OCT elastography.

Also disclosed herein is an exemplary system for acquiring and performing PSCD OCTA using the disclosed methods. The exemplary system comprises an OCT device configured to acquire OCT structural and angiography data in functional connection with a computing device having a logic subsystem and data holding capabilities. In embodiments the computing device is configured to receive data from the OCT device and perform one or more operations of the methods described herein.

In the following detailed description, reference is made to the accompanying drawings which form a part hereof, and in which are shown by way of illustration embodiments that can be practiced. It is to be understood that other embodiments can be utilized and structural or logical changes can be made without departing from the scope. Therefore, the following detailed description is not to be taken in a limiting sense, and the scope of embodiments is defined by the appended claims and their equivalents.

Various operations can be described as multiple discrete operations in turn, in a manner that can be helpful in understanding embodiments; however, the order of description should not be construed to imply that these operations are order dependent.

The description may use the terms "embodiment" or "embodiments," which may each refer to one or more of the same or different embodiments. Furthermore, the terms "comprising," "including," "having," and the like, as used with respect to embodiments, are synonymous.

In various embodiments, structure and/or flow information of a sample can be obtained using OCT (structure) and OCT angiography (flow) imaging-based on the detection of spectral interference. Such imaging can be two-dimensional (2-D) or three-dimensional (3-D), depending on the application. Structural imaging can be of an extended depth range relative to prior art methods, and flow imaging can be performed in real time. One or both of structural imaging and flow imaging as disclosed herein can be enlisted for producing 2-D or 3-D images.

Unless otherwise noted or explained, all technical and scientific terms used herein are used according to conventional usage and have the same meaning as commonly understood by one of ordinary skill in the art which the disclosure belongs. Although methods, systems, and apparatuses/materials similar or equivalent to those described herein can be used in the practice or testing of the present disclosure, suitable methods, systems, and apparatuses/materials are described below.

All publications, patent applications, patents, and other references mentioned herein are incorporated by reference in their entirety. In case of conflict, the present specification, including explanation of terms, will control. In addition, the methods, systems, apparatuses, materials, and examples are illustrative only and not intended to be limiting.

In order to facilitate review of the various embodiments of the disclosure, the following explanation of specific terms is provided:

A-scan: A reflectivity profile that contains information about spatial dimensions and location of structures within an item of interest. An A-scan is an axial scan directed along the optical axis of the OCT device and penetrates the sample being imaged. The A-scan encodes reflectivity information (for example, signal intensity) as a function of depth (z-direction).

B-scan: A cross-sectional tomograph that can be achieved by laterally combining a series of axial depth scans (i.e., A-scans) in the x-direction or y-direction. A B-scan encodes planar cross-sectional information from the sample and is typically presented as an image. Thus, a B-scan can be called a cross sectional image.

Dataset: As used herein, a dataset is an ordered-array representation of stored data values that encodes relative spatial location in row-column-depth (x-y-z axes) format. In the context of OCT, as used herein, a dataset can be conceptualized as a three dimensional array of voxels, each voxel having an associated value (for example, an intensity value, a complex value having both amplitude and phase information, a decorrelation value, or other signal representations). An A-scan corresponds to a set of collinear voxels along the depth (z-axis) direction of the dataset; a B-scan is made up of set of adjacent A-scans combined in the row or column (x- or y-axis) directions. Such a B-scan can also be referred to as an image, and its constituent voxels referred to as pixels. A collection of adjacent B-scans can be combined form a 3D volumetric set of voxel data referred to as a 3D image. In the system and methods described herein, the dataset obtained by an OCT scanning device is termed a "structural OCT" dataset whose values can, for example, be complex numbers carrying intensity and phase information. This structural OCT dataset can be used to calculate a corresponding dataset termed an "OCT angiography" dataset reflecting flow within the imaged sample. There is a correspondence between the voxels of the structural OCT dataset and the OCT angiography dataset. Thus, values from the datasets can be "overlaid" to present composite images of structure and flow (e.g., tissue microstructure and blood flow) or otherwise combined or compared.

En Face angiogram: OCT angiography data can be presented as a 2D projection of the three dimensional dataset onto a single planar image called an en face angiogram. Construction of such an en face angiogram requires the specification of the upper and lower depth extents that enclose the region of interest within the retina OCT scan to be projected onto the angiogram image. These upper and lower depth extents can be specified as the boundaries between different layers of the retina (e.g., the voxels between the inner limiting membrane and outer plexiform layer could be used to generate an en face angiogram of the inner retina). Once generated, the en face angiogram image may be used to quantify various features of the retinal vasculature as described herein. This quantification typically involves the setting of a threshold value to differentiate, for example, the pixels that represent flow within vasculature from static tissue within the angiogram. These en face angiograms can be interpreted in a manner similar to traditional angiography techniques such as fluorescein angiography (FA) or indocyanine green (ICG) angiography, and are thus well-suited for clinical use. It is also common to generate en face images from structural OCT data in a manner analogous to that used to generate en face angiograms. Angiograms from different layers may also be color-coded and overlaid to present composite angiograms with encoded depth information; structural en face images may also be included in such composite image generation.

Functional OCT, as used herein, broadly refers to the extension of OCT techniques to provide information beyond structural characterization. For example, whereas structural OCT imaging may be used to gather spatial information about a tissue's anatomical organization, functional OCT may be used to gather information about processes occurring within that tissue sample such as blood flow, tissue perfusion and oxygenation, birefringence, etc. Examples of functional OCT include, but are not limited to, OCT angiography (OCTA) and associated techniques for characterizing blood flow, Doppler OCT, polarization-sensitive OCT, OCT elastography, spectroscopic OCT, differential absorption OCT, and molecular imaging OCT.

The present inventors have previously described an efficient bulk motion phase compensation technique for spectral domain OCTA devices (see U.S. patent application Ser. No. 17/044,559 (hereinafter "the '559 application"), and X. Wei, A. Camino, S. Pi, W. Cepurna, D. Huang, J. C. Morrison, and Y. Jia, "Fast and robust standard-deviation-based method for bulk motion compensation in phase-based functional OCT," Optics letters 43, 2204-2207 (2018), hereinafter "Wei"). However, the fastest OCTA devices are swept-source, rather than spectral domain, instruments. And while the previous bulk motion phase compensation technique performed well in comparison to other state-of-the-art histogram-based phase compensation approaches, it may not be suitable for swept-source OCTA devices. The main issue is trigger jitter, a source of noise unique to swept-source devices in OCTA technology. Many phase compensation algorithms assume a constant phase across imaging depth, but the random electronic noise introduced by trigger jitter violates this assumption.

Various embodiments herein provide a PSCD OCTA technique. In embodiments, the PSCD OCTA technique may be used with any OCTA device, including swept-source instruments. Various embodiments also provide a new OCTA flow detection metric, which is referred to as phase-stabilized complex-decorrelation angiography (PSCDA). As demonstrated in example implementations described further below, PSCDA may efficiently produce clean, high dynamic range angiograms from multiple devices. The present disclosure also quantitatively and qualitatively benchmarks the performance of the PSCDA against two other leading OCTA processing techniques: split-spectrum amplitude-decorrelation angiography (SSADA) (see Y. Jia, O. Tan, J. Tokayer, B. Potsaid, Y. Wang, J. J. Liu, M. F. Kraus, H. Subhash, J. G. Fujimoto, and J. Hornegger, "Split-spectrum amplitude-decorrelation angiography with optical coherence tomography," Optics express 20, 4710-4725 (2012), hereinafter "Jia") and complex difference (CDIF) angiography.

FIG. 1 illustrates a process 100 for PSCDA in accordance with various embodiments. At 102, the process 100 may include receiving raw OCT spectrum (e.g., from an OCT instrument). At 104, the process 100 may include performing one or more operations on the raw OCT spectrum to obtain complex OCT data (e.g., a complex OCT image) at 106. The one or more operations may include one or more Fourier Transforms, such as Fast Fourier Transforms (FFTs). The one or more operations may additionally or alternatively include one or more other operations, such as one or more operations for dispersion compensation, conversion from wavelength to frequency representation, and/or wave number interpolation.

As shown at 108 of the process 100, the complex OCT data may include amplitude information, flow phase information, and motion phase information. The flow phase information may correspond to flow in the sample that is scanned by the OCT instrument. The motion phase information may correspond to bulk motion of the sample.

At 110, the process 100 may include performing phase compensation on the complex OCT data. The phase compensation may include bulk motion phase compensation to remove the motion phase information and thereby generate a bulk motion compensated OCT data at 112. The bulk motion compensated OCT data may include the amplitude information and flow phase information from the complex OCT data, but may not include the motion phase information. In some embodiments, the phase compensation may further include compensation for other types of unwanted phase information, such as trigger jitter phase information, as further discussed below.

At 114, the process 100 may include performing a complex decorrelation process on the bulk motion compensated OCT data to generate OCTA data at 116. The OCTA data may be used to generate one or more OCTA images. The OCTA images may be clean, high dynamic range images, and may be generated using a wider variety of OCT devices/techniques than prior techniques.

Figure 2A:
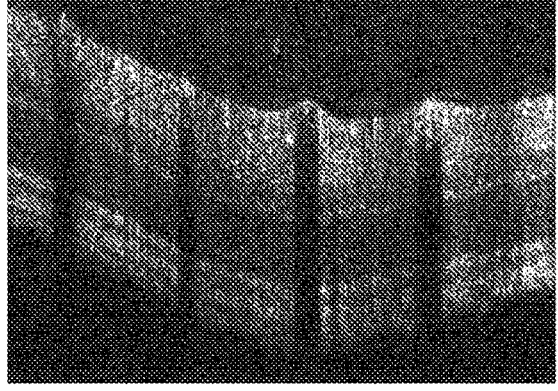
FIG. 2A illustrates an example of an OCT angiography (OCTA) image with bulk motion phase.
Figure 2B:
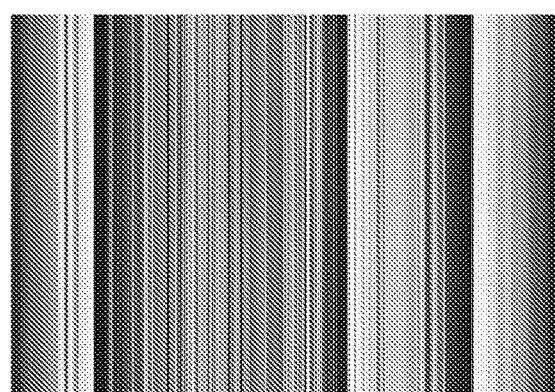
FIG. 2B illustrates an example image of bulk motion phase information in isolation.
Figure 2C:
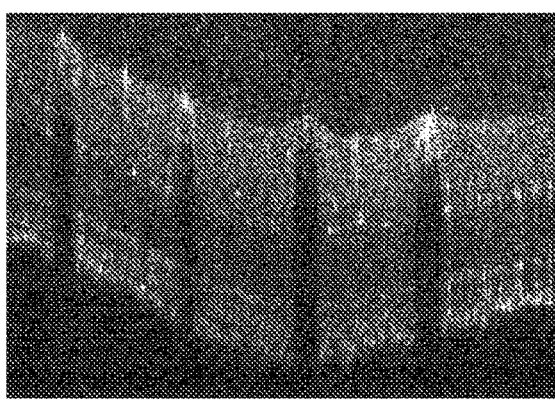
FIG. 2C illustrates an example of an OCTA image with bulk motion compensation (e.g., generated according to the process of FIG. 1), in accordance with various embodiments.

To illustrate the effectiveness of the process 100, FIG. 2A illustrates an example of an OCTA image with bulk motion phase; FIG. 2B illustrates an example image of bulk motion phase information in isolation; and FIG. 2C illustrates an example of an OCTA image with bulk motion compensation (e.g., generated according to the process 100).

Various aspects of the process 100 are described in more detail below.

Phase Stabilized Complex Decorrelation (PSCD)

In phase- and complex-based OCTA signal generation an effective means to stabilize the phase signal and remove phase noise can greatly improve the signal-to-noise ratio for flow detection. The phase portion of the spectral domain OCT signal may be represented as:

$$\phi(t, z) = \phi_P(t, z) + \phi_B(t, z) + \phi_M(t, z). \tag{1}$$

Here, $\phi_P$ is the phase shift caused by the moving red blood cells in vessels, $\phi_B$ is the bulk motion phase shift caused by involuntary motion, and $\phi_M$ is the system modulation phase shift (e.g., that is mainly contributed by the movement of the mechanical scanner). The $\phi_B(t, z)$ and $\phi_M(t, z)$ terms represent the phase noise that is desired to be removed; this can be accomplished with one of several phase compensation techniques (e.g., as described in S. Makita, Y. Hong, M. Yamanari, T. Yatagai, and Y. Yasuno, "Optical coherence angiography," Optics express 14, 7821-7840 (2006), hereinafter "Makita"; L. An and R. K. Wang, "In vivo volumetric imaging of vascular perfusion within human retina and choroids with optical microangiography," Optics express 16, 11438-11452 (2008), hereinafter "An"; and/or the techniques described by the present inventors in the '559 application and/or Wei). In the example implementations described herein, the technique described in the '559 application and/or Wei (developed by the inventors herein) is used. This technique provides a high-performance, robust standard-deviation-based bulk motion compensation method to remove the phase noise. The bulk motion phase may be calculated by using the pixel-wise standard deviation of the variance images constructed from two repeated scans with a tunable phase introduced, such as according to Equation (2):

$$\Delta\phi_{B+M} = a\tan2\left(\frac{v_1 - v_3}{v_2 - v_0}\right). \tag{2}$$

Here, the a tan 2 is the four-quadrant inverse tangent, and the variance $v_j$ is calculated according to:

$$v_j = std\left(\left|C_n(x, z) - C_{n+1}(x, z) \cdot \exp\left(-i \cdot j \cdot \frac{\pi}{2}\right)\right|\right)^2. \tag{3}$$

where std(•) is the standard deviation, C is the complex signal, $v_j$ is indexed by j, n is the scan index. This method can deliver a highly accurate bulk motion compensation result and requires minimal computational resources.

Phase stabilization is more complicated in swept source systems because trigger jitter in these instruments introduces an additional phase shift that must be corrected before bulk motion compensation. Compared to perfectly controlled triggering timing, the actual triggering time can randomly lead or lag a small amount of time $\Delta t$ (usually several nanoseconds), yielding a phase contribution of $$\phi_t(t, z) = \delta k \cdot z \tag{4}$$

for wavenumber k. To remove this contribution to the phase the averaged phase variance gradient may be calculated across each A-line to estimate $\delta k$ in Eq. 4, or the spectrum time shift between two repeated scans may be aligned (see G. Liu, O. Tan, S. S. Gao, A. D. Pechauer, B. Lee, C. D. Lu, J. G. Fujimoto, and D. Huang, "Postprocessing algorithms to minimize fixed-pattern artifact and reduce trigger jitter in swept source optical coherence tomography," Optics express 23, 9824-9834 (2015), hereinafter "Liu"; and S. Song, J. Xu, S. Men, T. T. Shen, and R. K. Wang, "Robust numerical phase stabilization for long-range swept-source optical coherence tomography," Journal of biophotonics 10, 1398-1410 (2017), hereinafter "Song"). The example implementations described herein use a spectrum-amplitude based method to remove the trigger jitter, as described in Liu.

After phase stabilization, either the phase- or complex-based OCTA signal may be extracted. Embodiments herein provide a novel phase-stabilized complex-decorrelation metric to extract the OCTA signal, as shown in Equation (5):

$$PSCD = \sum_{n=1}^{N-1} \frac{[A_n(x, z) + A_{n+1}(x, z)]^2 \cdot \theta_n(x, z)}{A_n^2(x, z) + A_{n+1}^2(x, z)}. \tag{5}$$

Here, $A_n$ and $A_{n+1}$ represent the amplitude signal from two repeated scans, and $\theta_n(x, z) = \varphi_n - \varphi_{n+1}$ represents the phase difference between two repeated scans. The phase difference between two repeated scans may be calculated according to:

$$\theta_n(x, z) = \left|a\tan\frac{imag(C_n(x, z) \cdot C_{n+1}(x, z)^*)}{real(C_n(x, z) \cdot C_{n+1}(x, z)^*)}\right|, \tag{6}$$

where $C_n$ and $C_{n+1}$ represent the complex signal from two repeated scans, a tan represents the inverse tangent, "imag" is the imaginary part of the complex variable, and "real" is the real part. By using this method, the amplitude signal is normalized according to the tissue reflectance, removing the reflectance dependence on the PSCD signal. The inclusion of the $\theta_n$ term may accurately account for system phase noise from both bulk motion and trigger jitter.

Comparison with Complex Difference Method

In complex difference (CDIF) methods the OCTA signal is generated by calculating the absolute difference between two repeated scans:

$$OCTA_{CD} = |C_n(x, z) - C_{n+1}(x, z)|. \tag{7}$$

Here, $C_n$ and $C_{n+1}$ are the complex signals generated from two repeated A-scans at the same location. In terms of amplitude $A_n(x, z)$ and the phase part $\phi_n(x, z)$, Equation (7) can be written as:

$$OCTA_{CD} = |A_n(x, z) \cdot \exp(i \cdot \phi_n(x, z)) - A_{n+1}(x, z) \cdot \exp(i \cdot \phi_{n+1}(x, z))| \tag{1}$$

$$OCTA_{CD} = \sqrt{A^2 + B^2 - 2AB \cdot \cos(\phi_n(x, z) - \phi_{n+1}(x, z))} \tag{2}$$

Figure 9:
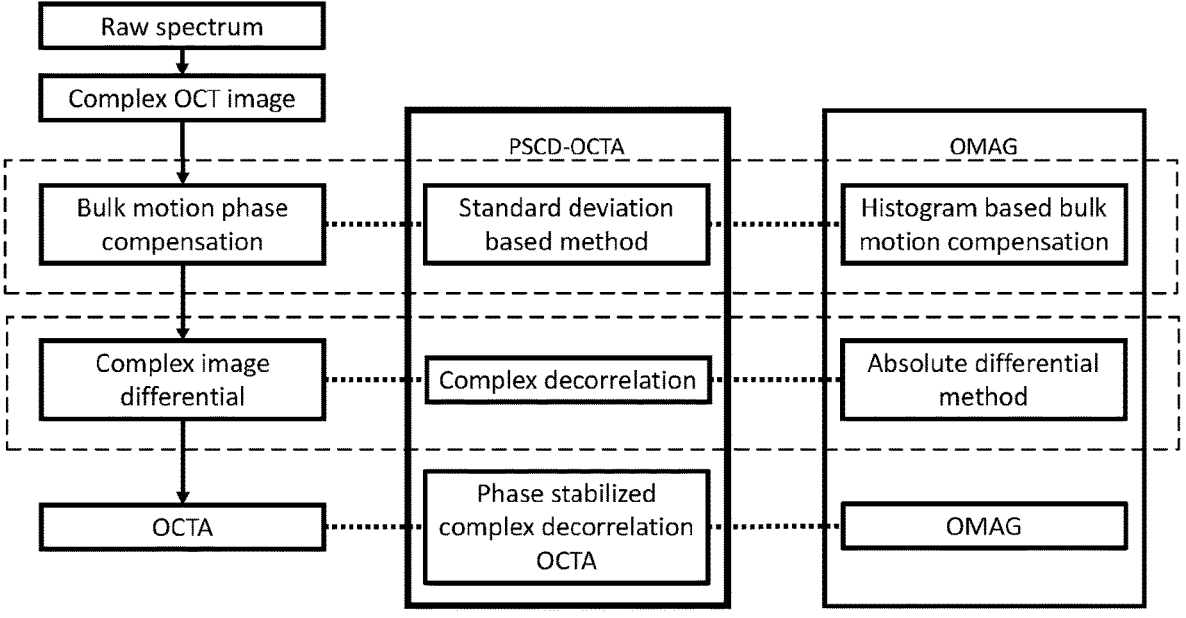
FIG. 9 illustrates a comparison of the PSCD process and an optical microangiography (OMAG) process, in accordance with various embodiments.

Optical microangiography (OMAG) is a prominent example of a CDIF approach. Like split-spectrum amplitude-decorrelation angiography (SSADA), it is an efficient OCTA algorithm that has been commercialized. FIG. 9 illustrates a comparison of the PSCD process and the OMAG process, in accordance with various embodiments.

Comparison with SSADA

Amplitude methods can also generate high quality OCTA images. SSADA applies multiple spectral splits to enhance the signal according to:

$$SSADA = 1 - \frac{1}{N-1}\frac{1}{M}\sum_{n=1}^{N-1}\sum_{m=1}^{M} \frac{A_n(x, z) \cdot A_{n+1}(x, z)}{\left[\frac{1}{2}A_n(x, z)^2 + \frac{1}{2}A_{n+1}(x, z)^2\right]}, \tag{10}$$

where $A_n(x, z)$ represents the n-th repeated OCT B-scan amplitude signal at position x and z, m represents m-th split spectrum. N represents the number of repeated scans at the same position and M represents the number of split spectrums. The example implementations described herein use 11 split spectrums, e.g., to maximally enhance the OCTA signal (see S. S. Gao, G. Liu, D. Huang, and Y. Jia, "Optimization of the split-spectrum amplitude-decorrelation angiography algorithm on a spectral optical coherence tomography system," Optics letters 40, 2305-2308 (2015), hereinafter "Gao").

Figure 10:
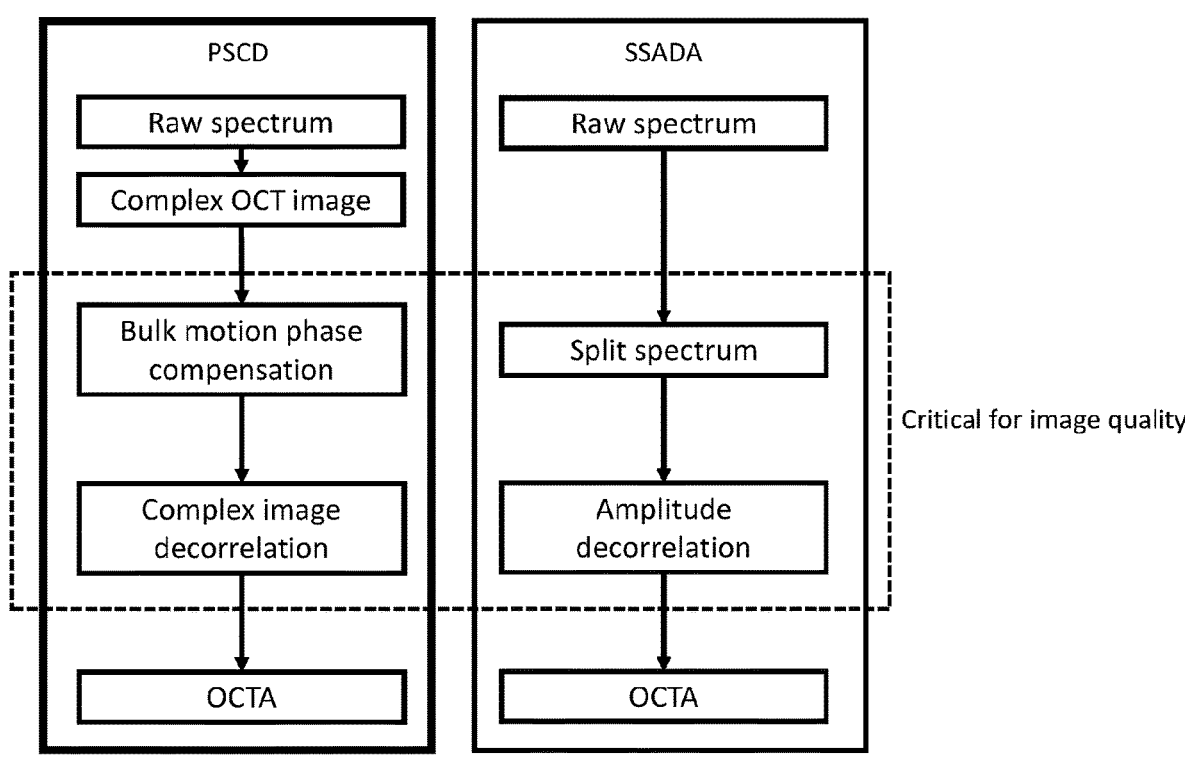
FIG. 10 illustrates a comparison of the PSCD process and a SSADA process, in accordance with various embodiments.

FIG. 10 illustrates a comparison of the PSCD process and the SSADA process, in accordance with various embodiments.

EXAMPLES

The following examples are illustrative of the disclosed methods. In light of this disclosure, those skilled in the art will recognize that variations of these examples and other examples of the disclosed method would be possible without undue experimentation.

As described in the examples, the dynamic range of the PSCD method has been studied using flow phantom experiment. A high dynamic range is achieved compared to the conventional complex OCTA algorithm. This method was tested using three different OCT systems, and image quality has been compared in three different algorithms. Quantitative analysis of the reflectance dependency was done by calculating the projected flow contrast on the RPE layer. Compared to the conventional complex OCTA algorithm, the PSCD OCTA method provides improved dynamic range and image quality, and the reflectance dependency has been suppressed.

Systems

The PSCD signal generation techniques described herein were tested using three different instruments. The first system (the "400-kHz system" hereafter) was a previously developed high-speed, wide-field swept-source OCT prototype (see X. Wei, T. T. Hormel, Y. Guo, and Y. Jia, "75-degree non-mydriatic single-volume optical coherence tomographic angiography," Biomedical Optics Express 10, 6286-6295 (2019). A 400-kHz "ping-pong" laser (Axsun Technologies Inc.) with a center wavelength of 1060 nm with a 100 nm bandwidth was used. The system provides a lateral resolution of 10 µm and axial resolution of 5 µm. Graphics processing unit (GPU)-based real-time OCT/OCTA data processing software was also developed for the system (see X. Wei, A. Camino, S. Pi, T. T. Hormel, W. Cepurna, D. Huang, J. C. Morrison, and Y. Jia, "Real-time cross-sectional and en face OCT angiography guiding high-quality scan acquisition," Optics letters 44, 1431-1434 (2019), hereinafter "Wei 2"). The software also integrated a OCTA based self-tracking method (see X. Wei, T. T. Hormel, Y. Guo, T. S. Hwang, and Y. Jia, "High-resolution wide-field OCT angiography with a self-navigation method to correct microsaccades and blinks," Biomedical Optics Express 11, 3234-3245 (2020), hereinafter "Wei 3") to remove blinks and microsaccades by rescanning the artifact-affected area in real-time. A 75-degree field of view can be achieved with this system.

The second OCT system (referred to herein as the "visible-light system") is a 50-kHz spectral domain prototype primarily developed for rodent imaging (see S. Pi, A. Camino, W. Cepurna, X. Wei, M. Zhang, D. Huang, J. Morrison, and Y. Jia, "Automated spectroscopic retinal oximetry with visible-light optical coherence tomography," Biomedical optics express 9, 2056-2067 (2018), hereinafter "Pi"), working in the visible band with a center wavelength of 560 nm and a 100 nm bandwidth. The system provides 1.2 µm axial resolution and 6-µm lateral resolution. GPU-based OCT/OCTA data acquisition software was also developed for the system to monitor the OCT and OCTA image quality in real-time (see Wei 2).

The performance of the technique was also assessed on a commercial 70-kHz spectral domain OCT system (RTVue-XR Avanti; Optovue, Inc., Fremont, CA; referred to herein as the "commercial system"). This system has a center wavelength of 840 nm, axial resolution of 5 µm and lateral resolution of 10 µm. All the experimental procedures were approved by Oregon Health and Science University's (OHSU) Institutional Review Board/Ethics Committee.

Example Experiments

Flow Phantom Experiment

A flow phantom setup has been made using 250-µm inner diameter clear glass tubing (e.g., similar to the setup described in X. Wei, T. T. Hormel, S. Pi, Y. Guo, Y. Jian, and Y. Jia, "High dynamic range optical coherence tomography angiography (HDR-OCTA)," Biomedical optics express 10, 3560-3571 (2019), hereinafter "Wei 4"). A syringe pump enables controlled flow variation in the tubing with speeds ranging from 0 to 6 mm/s. Bovine blood was used as the fluid in these experiments. All flow phantom data was acquired with the 400-kHz system described above (e.g., 400-kHz swept source OCT system).

Rodent Imaging

Brown Norway rats were first anesthetized in a sealed chamber with 5% isoflurane for 10 minutes. During the imaging session, oxygen gas with 2.5% isoflurane at a flow rate of 1 L/min is used for inhalation. The exhaust isoflurane is absorbed using a gas filter (OMNICON F/air, Bickford). The animal body temperature is maintained using 38.5° C. using a water-warming blanket. All the experimental procedures were approved by the Institutional Animal Care and Use Committee (IACUC) of OHSU. 2.1×2.1-mm OCT scan volumes were acquired. 512 A-lines were sampled to obtain a single B-scan. Three repeated B-scans were captured at a fixed position before proceeding to the next sampling location. A total of 512 locations were scanned. Two different complex-based OCTA algorithms and the amplitude-based SSADA algorithm were used to process the same scans. The brightness and contrast of these images were adjusted by normalize using the pixel value between 5% to 95% of the total pixels value. En face OCT reflectance images were also generated.

Human Imaging

Fourteen patients' eyes were imaged using a 70-kHz commercial OCT system. These images were acquired by a professional OCT operator. The image size is 3×3 mm, centered at the fovea. Each contains 304 A-lines in each B-scan, and each A-line contained 2048 pixels. Three repeated B-scans were acquired at each cross-sectional position. A total of 304 positions were scanned across the total 3 mm scanning length. Raw spectrum data were acquired and processed using PSCD, CDIF and SSADA OCTA algorithms. The generated OCT and OCTA images were segmented using the automatic segmentation software described in M. Zhang, J. Wang, A. D. Pechauer, T. S. Hwang, S. S. Gao, L. Liu, L. Liu, S. T. Bailey, D. J. Wilson, and D. Huang, "Advanced image processing for optical coherence tomographic angiography of macular diseases," Biomedical Optics Express 6, 4661-4675 (2015), hereinafter "Zhang." En face OCTA images were then generated using maximum projection (see T. T. Hormel, J. Wang, S. T. Bailey, T. S. Hwang, D. Huang, and Y. Jia, "Maximum value projection produces better en face OCT angiograms than mean value projection," Biomedical optics express 9, 6412-6424 (2018), hereinafter "Hormel"). A custom color map was applied to better illustrate the OCTA image.

Results

Phase Stabilization

To verify the performance of the phase stabilization performance in the PSCD method described herein, flow phantom and human retinal images were acquired using the 400 k Hz system. First, an uncompensated phase variance image was generated. The phase variance images are calculated directly using two complex OCT images acquired at the same lateral position. Both the flow phantom image (FIG. 3A) and the wide-field retinal image (FIG. 3B) contain significant phase noise. The major noise contributions to the flow phantom image are from the system modulation caused by the rotation of the galvo scanner and from trigger jitter. The reflectance signal in flow phantom experiments is small due to the low reflectivity of the materials, which causes it to be dominated by noise. The random phase background noise level is therefore high in the flow phantom phase variance data. Phase noise in the retinal image also includes a contribution from involuntary subject movement (e.g. due to ocular pulsation).

After applying the phase stabilization algorithm in the PSCD method, both the phase stabilized flow phantom (FIG. 3C) and retinal phase variance images (FIG. 3D) have an even phase background that is close to zero. Our algorithm can effectively remove the background phase noise even when it is large. This effectiveness can be demonstrated using an axial averaged phase plot as shown in FIGS. 3A-3D.

Dynamic Range

The dynamic range of flow detection is a key parameter in OCTA technology that is controlled by both the device's scanning interval pattern and the OCTA generating algorithm. To assess the dynamic range of the proposed PSCD method, a flow phantom experiment was performed. For comparison's sake, the data was also processed using the CDIF technique (e.g., as described in L. An, J. Qin, and R. K. Wang, "Ultrahigh sensitive optical microangiography for in vivo imaging of microcirculations within human skin tissue beds," Optics express 18, 8220-8228 (2010)). Due to significant OCTA signal difference between complex and amplitude-based methods, the SSADA method was not included in the comparison. The flow phantom apparatus was placed with a small angle to the perpendicular direction of the scanning laser beam. The OCT sample beam was scanned across a 1 mm wide cross-section of the glass tubing. 300 A-lines were acquired for each B-scan, and a total of 128 continuous B-scans were acquired from this single position. The OCTA image were generated using the adjacent B-scans with a scanning interval of 1.5 ms.

Figures 3A, 3B, 3C, 3D:
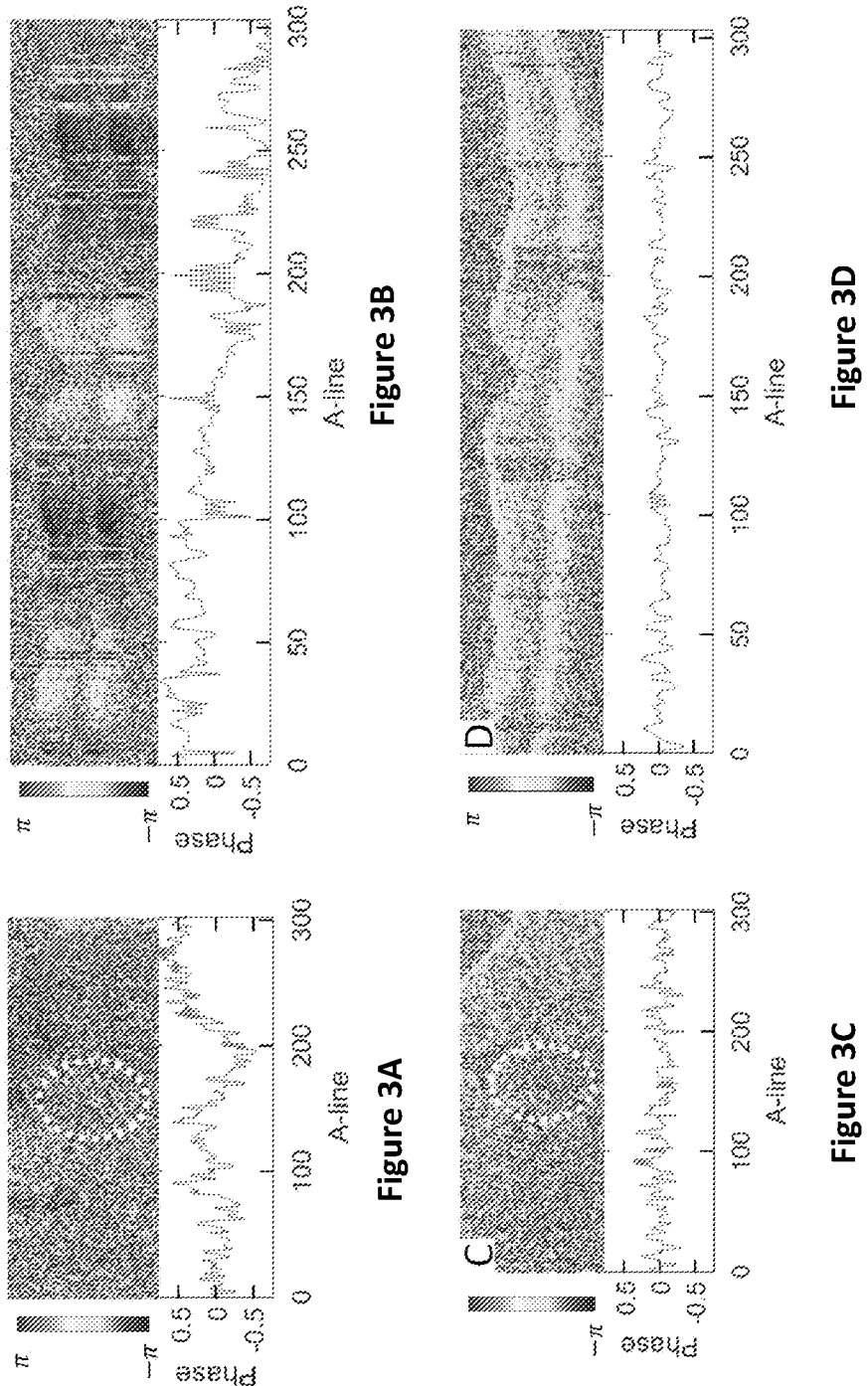
FIGS. 3A-3D illustrate phase variance plots before and after applying the phase stabilization method.
Figures 4A, 4B, 4C, 4D, 4E:
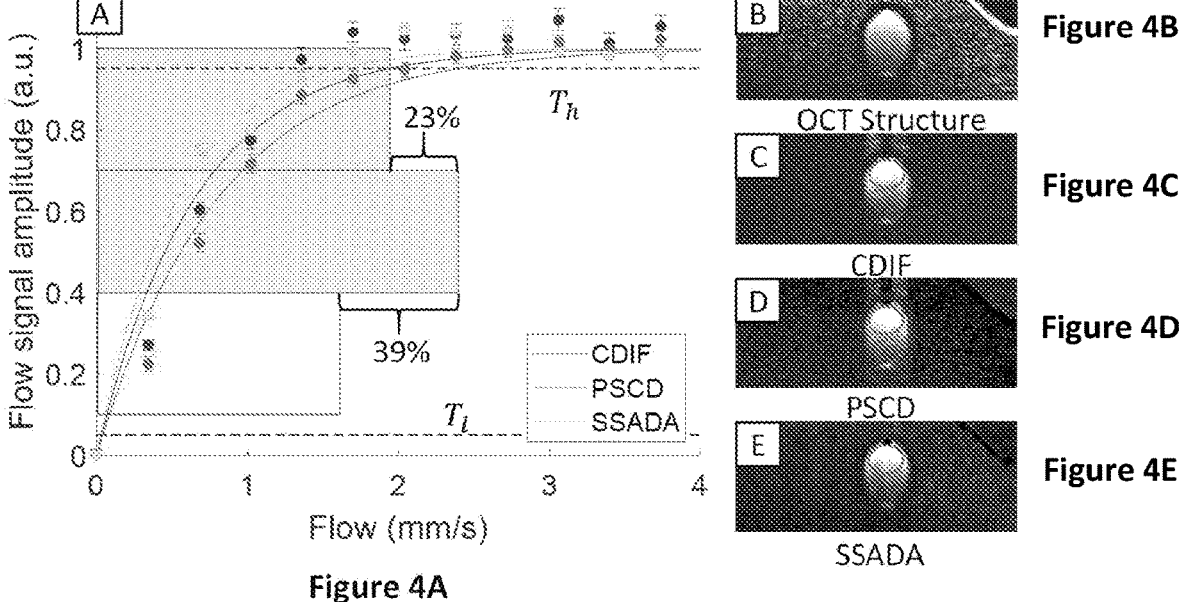
FIGS. 4A-4E illustrate flow phantom results between three different OCTA algorithms.

The PSCD, CDIF, and SSADA methods can all highlight the flow signal in the flow phantom and remove the static background signal (see FIGS. 3C, 3D, 3E). Both of the complex algorithms used the same standard deviation based bulk motion compensation algorithm to remove the system modulation phase shift (see Wei). While there is no involuntary bulk motion in flow phantoms, the set up is very sensitive to phase shifts induced by vibration. Data where this effect was large were excluded from the analysis. OCTA flow signal was averaged inside the red circle in FIGS. 4C, 4D, and 4E for all three techniques in order to calculate the dynamic range. In each dataset, a total of 50 averaged OCTA values were calculated for the flow rates between 0 mm/s to 6 mm/s. The values were normalized to a range of 0 to 1 using the maximum and minimum value in each dataset. The dynamic range is defined as the 90% in between the minimum and maximum value. A high threshold $T_h$ and low threshold $T_l$ is defined as 0.95 and 0.05, respectively. Using the PSCD method, the dynamic range of the flow detection has been improved by 39% compared to the SSADA method and 23% compared to the CDIF method.

Rodent Imaging

PSCD, CDIF and SSADA all can generate high quality OCTA images. However, by comparing the back ground noise, the inventors noticed that the CDIF method has a higher reflectance dependency, this is due to the lack of intensity normalization in the OCTA algorithm. There is also some variation in image quality. In the SVP layer en face images (FIGS. 4A, 4D, 4G) noise levels in the complex-based methods appear larger compared to SSADA. In the DCP layer, the PSCD and CDIF methods appear to have less noise (note the lower background in FIGS. 5A-5F for PSCD and CDIF) compared to SSADA method (see FIGS. 5G-5I).

Imaging Using Commercial OCT System

Figures 5A, 5B, 5C, 5D, 5E, 5F, 5G, 5H, 5I, 5J, 5K, 5L:
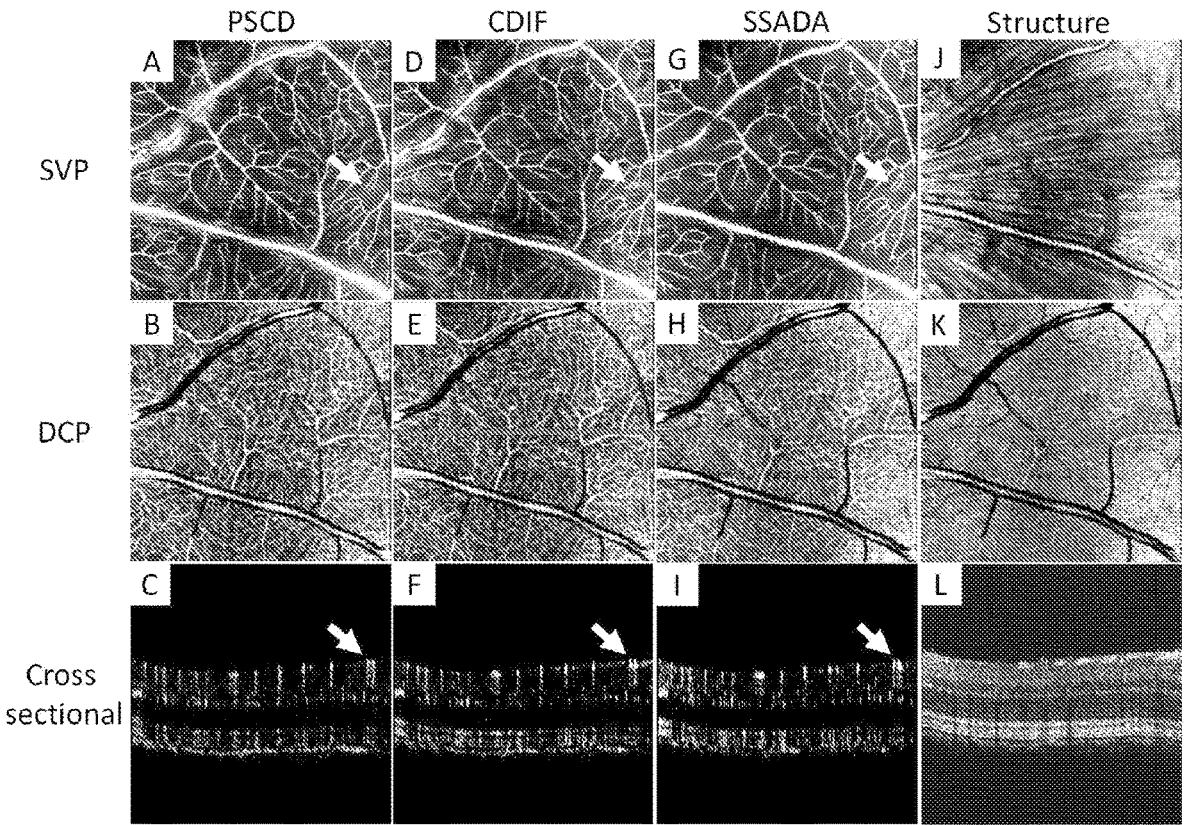
FIGS. 5A-5L illustrate OCTA images of a rat retina acquired with a visible light system compared between different algorithms. First row (FIGS. 5A, 5D, 5G, 5J: superficial vascular plexus (SVP) en face images; second row (FIGS. 5B, 5E, 5H, 5K): deep capillary plexus (DCP) en face images; third row (FIGS. 5C, 5F, 5I, 5L): cross-sectional images selected from the same OCT/OCTA volume at the position indicated by the blue line. The CDIF method has a higher reflectance dependency, which can be observed by considering region with a high reflectance background (white arrows in FIGS. 5D and 5F) than the PSCD and split-spectrum amplitude decorrelation angiography (SSADA) method (white arrows in FIGS. 5A, 5C, 5G, 5I).
Figures 6A, 6O:
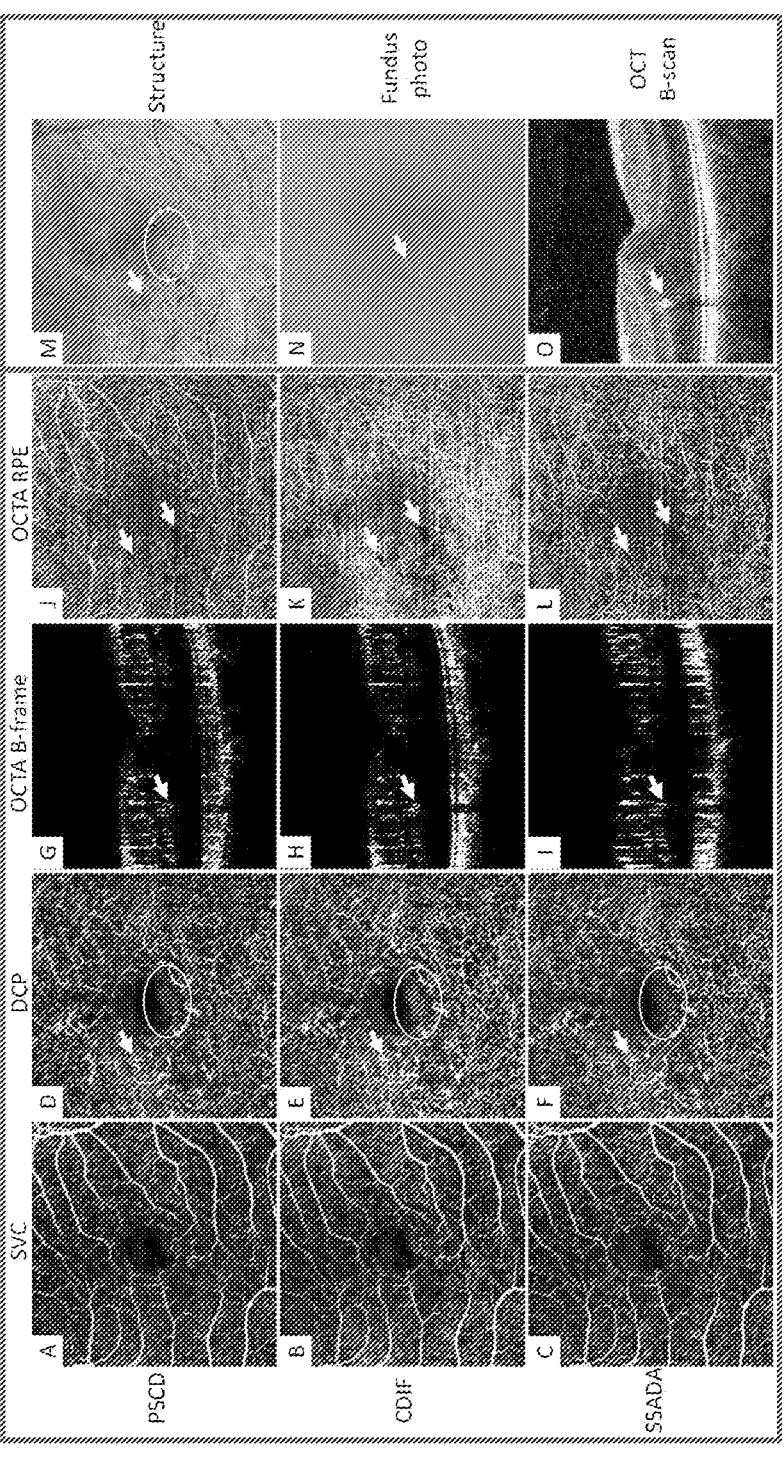
FIGS. 6A-6O illustrate OCTA image comparison between the PSCD, CDIF, and SSADA methods using 3×3 mm images of an eye with diabetic retinopathy (DR). White arrows and white circles indicate the hard exudate and cystic fluid. The hard exudate and cystic fluid have higher intensity in images generated using CDIF method than the other two methods. Compared with other two methods (FIGS. 6J, 6L), the background noise is higher in CDIF RPE OCTA en face projection images (FIG. 6K). The CDIF method (FIGS. 6E, 6H, 6K) has higher reflectance dependency than the other two methods (FIGS. 6D, 6G, 6J, 6F, 6I, 6L).

Using commercial OCT system, all three algorithms can generate high quality OCTA images (FIG. 6). Large vessels and capillaries can be observed in three different vascular plexuses. Flow signal can also be clearly observed in B-frames (FIGS. 5G, 5H, 5I). However, there are some difference that can be observed in the portrayal of pathologies. This patient imaged in FIG. 6 has hard exudates that can be clearly observed from the fundus photo (FIG. 6K), OCT structural en face (FIG. 6J) and B-scans (FIG. 6L). These hard exudates are high reflectance tissues without any blood flow. Due to lack of reflectance normalization, images generated using the CDIF method (FIGS. 6E, 6H) have artificial flow signal compare with PSCD (FIG. 6D, 6G) and SSADA (FIG. 6F, 6I) methods. In this case, cysts with fluid that contains hyperreflective particles can also be observed in FIGS. 6D, 6E, and 6F). Images generated using CDIF also have higher reflectance dependence in flow signal than the other two methods.

Figures 7A, 7B, 7C, 7D, 7E, 7F, 7G:
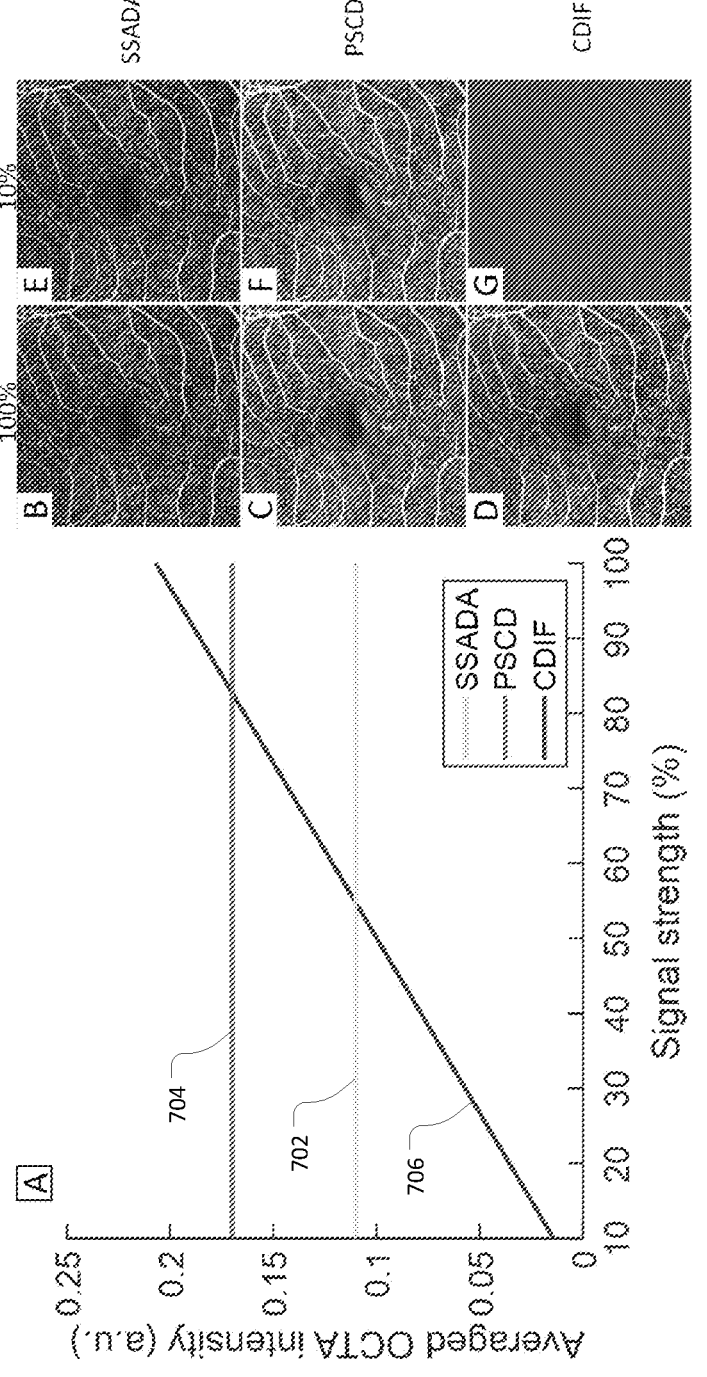
FIGS. 7A-7G illustrate reflectance dependency on averaged OCTA signal intensity. Averaged OCTA signal intensity is calculated and plotted from en face inner retina images generated by three different OCTA methods (see FIG. 7A). SSADA and PSCD methods have no correlation with the OCT signal intensity and CDIF method has high correlation with the OCT signal intensity.

The OCTA reflectance dependency can also be evaluated quantitatively, e.g., as shown in FIGS. 7A-7G. For example, the spectrum amplitude may be numerically reduced from 100% to 10%. At every 10% reduction point, OCTA images were generated using all three different methods. En face inner retina angiograms are generated using maximum projection. The images were normalized to values from 0 to 1 according to the minimum and maximum flow pixel values generated by each method in the simulated dataset. Averaged OCTA signal intensity was calculated by averaging all pixels in the en face image. In FIG. 7A, line 702 corresponds to SSADA, line 704 corresponds to PSCD, and line 706 corresponds to CDIF. Due to the normalization process embedded in the decorrelation step, there is no OCTA intensity change when using PSCD or SSADA methods. However, for the CDIF method, there is a strong signal intensity dependency (line 706 in FIG. 7A).

Imaging Using 400-kHz Widefield OCT System

Figures 8A, 8B, 8C, 8D, 8E:
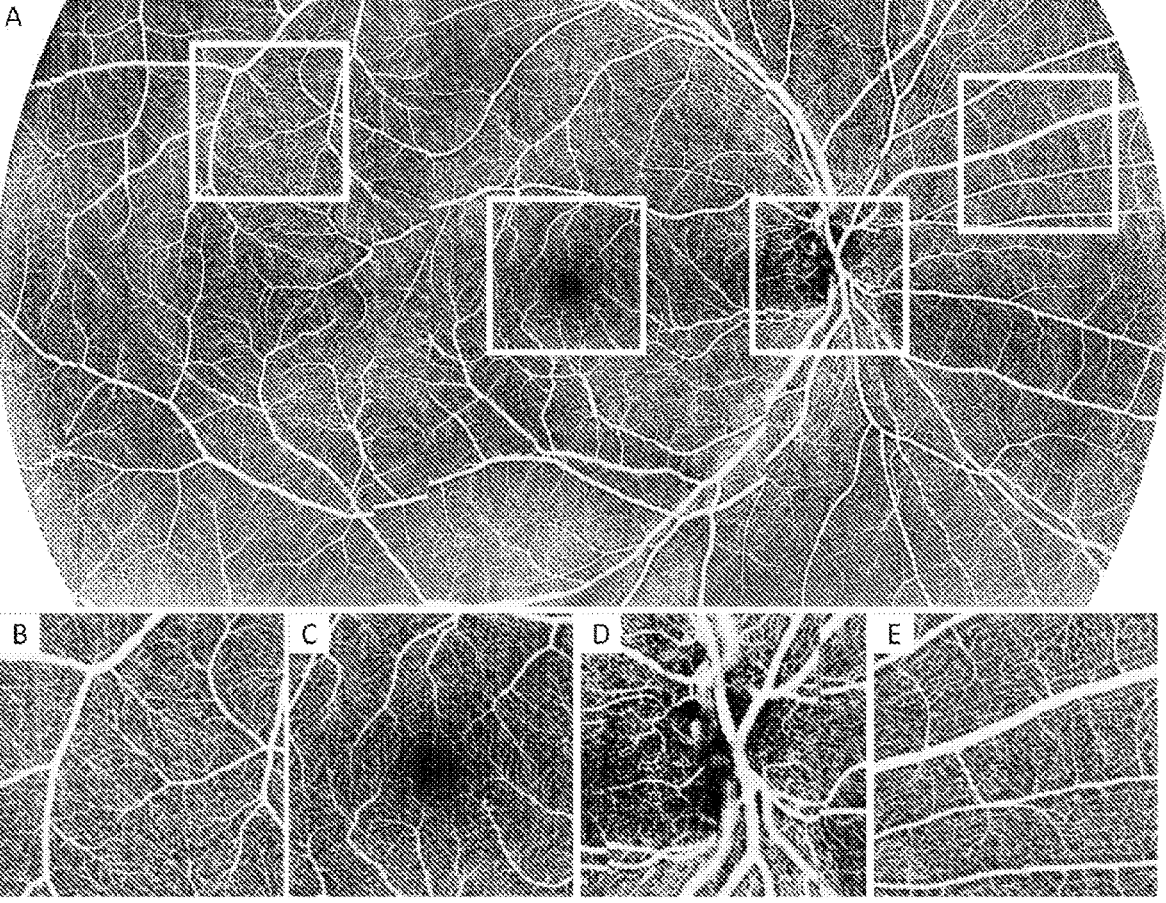
FIGS. 8A-8E illustrate a wide-field PSCD OCTA image acquired from a healthy subject.

Healthy subjects and patients with diabetic retinopathy were imaged using the 400 kHz system. For each A-line in the image, 1536 spectrum samples were recorded, which is equivalent to 4 mm imaging depth. Each B-scan contains 1232 A-lines, and three repeat B-scans were acquired. A total of 2304 cross-sectional positions were scanned across the 23 mm lateral imaging range. During the data acquisition, imaging subjects are encouraged to blink to facilitate formation of an even tear film. The total data acquisition time is less than one minute. Raw spectrum data was acquired and processed using MATLAB (The MathWorks, Inc.). The PSCD method was applied to extract OCTA signals. The OCT and OCTA data were segmented using automatic segmentation software (see Y. Guo, A. Camino, M. Zhang, J. Wang, D. Huang, T. Hwang, and Y. Jia, "Automated segmentation of retinal layer boundaries and capillary plexuses in wide-field optical coherence tomographic angiography," Biomedical optics express 9, 4429-4442 (2018)). The inner retinal en face OCTA image was generated using maximum projection (FIG. 8A). In the en face image, both large vessels and capillaries are clearly visible (FIGS. 8B-8E). However, due to the lack of active tracking, the passive self-tracking method used by this instrument cannot correct some motion caused vessel disruptions.

Further Discussion of PSCD Angiography and Experimental Results

As discussed above, various embodiments herein provide a PSCD angiography technique to generate high quality OCTA images. This technique may incorporate an efficient and accurate phase stabilization step using standard deviation method, and may be used on either spectral domain or swept source OCT systems. By assessing it on OCTA scans generated by a flow phantom, it is shown herein that the PSCD method provides extended dynamic range than conventional CDIF method and SSADA method. By assessing the PSCD on rodent, and human OCTA scans collected on three different OCTA devices, the experimental results described herein show the superior performance of PSCD method on suppressing flow artifacts attributed by high reflectance tissue, such as hard exudates and cystic fluid with hyper-reflective materials, and RPE.

A quantitative dynamic range study with a flow phantom experiment is also described herein. These experiments indicate that the PSCD approach increased the dynamic range of flow detection by 23% in comparison to the CDIF method and 39% in comparison to the SSADA method. In the results, the complex methods PSCD and CDIF have a higher dynamic range than the amplitude-based method SSADA. In the complex based method, both the amplitude and phase components contribute the OCTA signal and extended dynamic range, but in the amplitude-based method, the amplitude component is the sole contributor to the OCTA signal dynamic range. Because of this, the additional phase contribution in the complex method increases the dynamic range of both the PSCD and CDIF method. Computational decisions may account for the remaining difference in dynamic range between the CDIF and PSCD methods. In the CDIF method, the OCTA signal is generated by calculating the absolute value of the complex difference. The amplitude difference and phase difference are integrated and combined into the complex difference (see Equation 9). Whereas, in PSCD, the phase difference is calculated separately and the phase difference contrast is boosted by the amplitude signal (see Equation 5). By doing this, PSCD method can be more sensitive to slow flow. For fast flow in large vessels, the phase difference is high due to the increased flow speed. Thus, the dynamic range of flow signal in PSCD method is wider than that of CDIF method.

In the in vivo studies presented here, OCTA images with exceptional quality have been acquired from both prototype systems and a commercial OCT system. From these images, it is found that both a conventional complex difference CDIF algorithm, SSADA, and the PSCD method described herein can generate high quality OCTA image with resolution capable of capturing capillary-scale microvasculature. However, the PSCD method has less reflectance dependency, which can remove noise attributable to hyper-reflective tissues, and both the animal and human images show an improvement in image clarity.

For any existing or future OCTA algorithm, one should be aware of the necessity of the evaluation of reflectance (or OCT signal) independency. If OCTA signal is high when OCT signal is high, the false positive flow can be visualized on angiograms or detected by quantitative measurements. For instance, nerve fiber layer and retinal pigment epithelium are more vulnerable to this type of artifact due to their higher reflectance than other layers in healthy retina; hyper-reflective materials (such as neovascular tissue, fibrosis, exudate, hemorrhage, drusen and hyper-reflective particles in cystic pockets) in macular diseases can also induce the artificial flow. On the other hand, if OCTA signal is low when OCT signal is low, the false nonperfusion region can be generated, which also make the angiograms indecipherable. It is inevitable to encounter the imaging conditions such as vignetting and defocusing, and eye conditions such as cataract, floater, and tear film break-up in clinical setting. Therefore, an OCTA algorithm that can be less affected by OCT signal strength will be more acceptable.

To quantitatively evaluate the reflectance dependency, the three methods were applied on a dataset with signal attenuated on the degree of 0.1-1 of original signal strength. Both PSCD and SSADA methods have no reflectance dependency due to the OCT signal normalization induced by the decorrelation step in OCTA computation. In contrast, the CDIF method has a high reflectance dependency. Compared to SSADA, the PSCD algorithm has better capillary contrast in the deep retinal layers. However, due to the increased sensitivity of complex methods, the superficial layer may have more background noise than SSADA. It should be noted that OCTA signal intensity (e.g., the mean value of OCTA signal on en face inner retinal angiograms) used for evaluation is not only affected by the intensity of the spectrum. It may also be affected by the signal to noise ratio of the spectrum. In the simulation described herein, only the spectrum intensity was numerically attenuated and the signal to noise ratio remained constant. Doing so allowed investigation of the effect of the reflectance signal on OCTA flow signal generation in isolation.

Besides the performance difference between OCTA algorithms, bulk motion compensation algorithm is more critical for complex OCTA image quality and computational efficiency. In the inventors' prior standard deviation-based bulk motion method (e.g., described in the '559 patent and Wei), the computation speed and image quality was compared between different bulk motion compensation algorithms. The standard deviation-based bulk motion method can provide a swift computation speed and high image quality. In the example experiments described herein, to better compare the OCTA algorithms, the previously developed standard deviation based bulk motion compensation algorithm was applied. By combining the PSCD technique and standard deviation based bulk motion compensation algorithm, the method can provide better image quality and computational efficiency, and it is more suitable for real-time applications.

It is noted that, in addition to the OCTA signal processing techniques explored in this disclosure, hardware considerations in OCTA devices will also affect the flow signal detection. To achieve an unbiased comparison, the flow signal was generated from the same raw spectrum acquired in each experiment using the three different approaches discussed above.

Additionally, the OCTA signal used in the PSCD method may be correlated to the phase shift. Accordingly, if the phase shift is equal or close to zero the OCTA value will still be suppressed even in the presence of speckle variance. However, in reality, due to the long inter B-scan time, the chance of getting a small phase shift is minimal, so the final image quality should not be significantly adversely affected.

Optical Coherence Tomography Angiography Image Processing System

Figure 11:
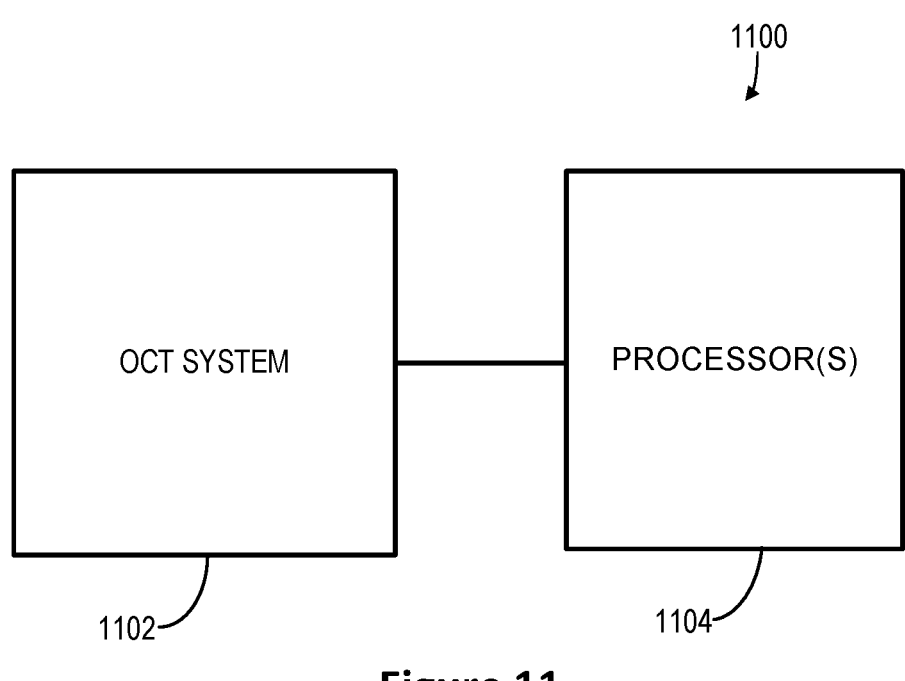
FIG. 11 schematically shows an example system for processing OCT and OCTA datasets in accordance with the disclosure.

FIG. 11 schematically shows an example system 1100 for OCT image processing in accordance with various embodiments. In embodiments, the system 1100 may correspond to one or more of the three OCT systems used in the example systems and/or experiments described above. System 1100 comprises an OCT system 1102 configured to acquire an OCT image comprising OCT interferograms and one or more processors or computing systems 1104 that are configured to implement the various processing routines described herein. OCT system 1100 can comprise an OCT system suitable for structural OCT and OCT angiography applications, e.g., a swept source OCT system or spectral domain OCT system.

In various embodiments, an OCT system can be adapted to allow an operator to perform various tasks. For example, an OCT system can be adapted to allow an operator to configure and/or launch various ones of the herein described methods. In some embodiments, an OCT system can be adapted to generate, or cause to be generated, reports of various information including, for example, reports of the results of scans run on a sample.

In embodiments of OCT systems comprising a display device, data and/or other information can be displayed for an operator. In embodiments, a display device can be adapted to receive an input (e.g., by a touch screen, actuation of an icon, manipulation of an input device such as a joystick or knob, etc.) and the input can, in some cases, be communicated (actively and/or passively) to one or more processors. In various embodiments, data and/or information can be displayed, and an operator can input information in response thereto.

In some embodiments, the above described methods and processes can be tied to a computing system, including one or more computers. In particular, the methods and processes described herein, e.g., the method 100 depicted in FIG. 1, described above, can be implemented as a computer application, computer service, computer API, computer library, and/or other computer program product.

Figure 12:
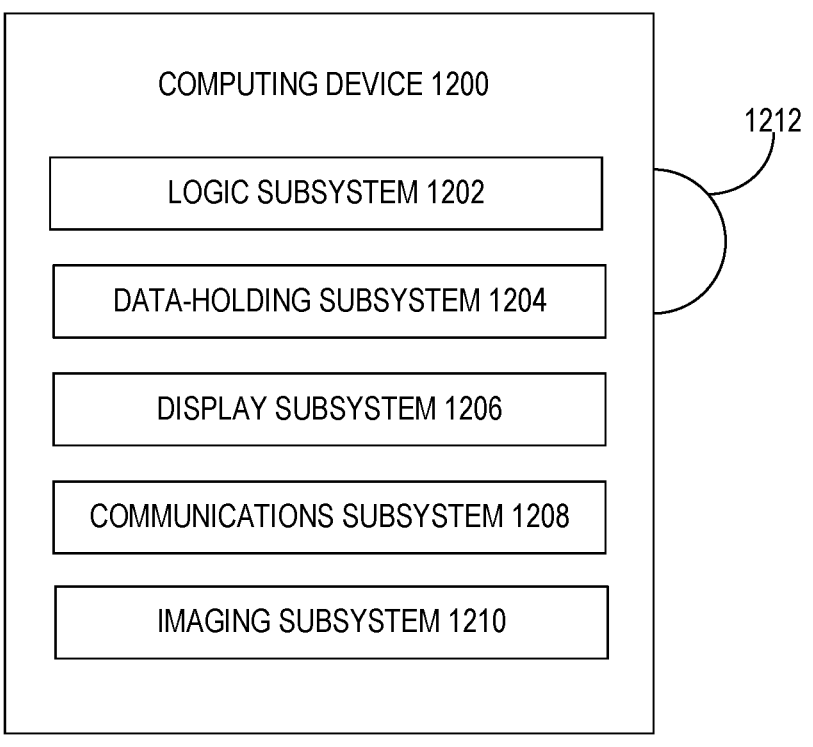
FIG. 12 schematically shows an example of a computing system in accordance with the disclosure.

FIG. 12 schematically shows a non-limiting computing device 1200 that can perform one or more of the above described methods and processes. For example, computing device 1200 can represent a processor included in system 1100 described above, and can be operatively coupled to, in communication with, or included in an OCT system or OCT image acquisition apparatus. Computing device 1200 is shown in simplified form. It is to be understood that virtually any computer architecture can be used without departing from the scope of this disclosure. In different embodiments, computing device 1200 can take the form of a microcomputer, an integrated computer circuit, printed circuit board (PCB), microchip, a mainframe computer, server computer, desktop computer, laptop computer, tablet computer, home entertainment computer, network computing device, mobile computing device, mobile communication device, gaming device, etc.

Computing device 1200 includes a logic subsystem 1202 and a data-holding subsystem 1204. Computing device 1200 can optionally include a display subsystem 1206, a communication subsystem 1208, an imaging subsystem 1210, and/ or other components not shown in FIG. 12. Computing device 1200 can also optionally include user input devices such as manually actuated buttons, switches, keyboards, mice, game controllers, cameras, microphones, and/or touch screens, for example.

Logic subsystem 1202 can include one or more physical devices configured to execute one or more machine-readable instructions. For example, the logic subsystem can be configured to execute one or more instructions that are part of one or more applications, services, programs, routines, libraries, objects, components, data structures, or other logical constructs. Such instructions can be implemented to perform a task, implement a data type, transform the state of one or more devices, or otherwise arrive at a desired result.

The logic subsystem can include one or more processors that are configured to execute software instructions. For example, the one or more processors can comprise physical circuitry programmed to perform various acts described herein. Additionally or alternatively, the logic subsystem can include one or more hardware or firmware logic machines configured to execute hardware or firmware instructions. Processors of the logic subsystem can be single core or multicore, and the programs executed thereon can be configured for parallel or distributed processing. The logic subsystem can optionally include individual components that are distributed throughout two or more devices, which can be remotely located and/or configured for coordinated processing. One or more aspects of the logic subsystem can be virtualized and executed by remotely accessible networked computing devices configured in a cloud computing configuration.

Data-holding subsystem 1204 can include one or more physical, non-transitory, devices configured to hold data and/or instructions executable by the logic subsystem to implement the herein described methods and processes. When such methods and processes are implemented, the state of data-holding subsystem 1204 can be transformed (e.g., to hold different data).

Data-holding subsystem 1204 can include removable media and/or built-in devices. Data-holding subsystem 1204 can include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 1204 can include devices with one or more of the following characteristics: volatile, nonvolatile, dynamic, static, read/write, read-only, random access, sequential access, location addressable, file addressable, and content addressable. In some embodiments, logic subsystem 1202 and data-holding subsystem 1204 can be integrated into one or more common devices, such as an application specific integrated circuit or a system on a chip.

FIG. 12 also shows an aspect of the data-holding subsystem in the form of removable computer-readable storage media 1212, which can be used to store and/or transfer data and/or instructions executable to implement the herein described methods and processes. Removable computer-readable storage media 1212 can take the form of CDs, DVDs, HD-DVDs, Blu-Ray Discs, EEPROMs, flash memory cards, USB storage devices, and/or floppy disks, among others.

When included, display subsystem 1206 can be used to present a visual representation of data held by data-holding subsystem 1204. As the herein described methods and processes change the data held by the data-holding subsystem, and thus transform the state of the data-holding subsystem, the state of display subsystem 1206 can likewise be transformed to visually represent changes in the underlying data. Display subsystem 1206 can include one or more display devices utilizing virtually any type of technology. Such display devices can be combined with logic subsystem 1202 and/or data-holding subsystem 1204 in a shared enclosure, or such display devices can be peripheral display devices.

When included, communication subsystem 1208 can be configured to communicatively couple computing device 1200 with one or more other computing devices. Communication subsystem 1208 can include wired and/or wireless communication devices compatible with one or more different communication protocols. As non-limiting examples, the communication subsystem can be configured for communication via a wireless telephone network, a wireless local area network, a wired local area network, a wireless wide area network, a wired wide area network, etc. In some embodiments, the communication subsystem can allow computing device 1200 to send and/or receive messages to and/or from other devices via a network such as the Internet.

When included, imaging subsystem 1210 can be used acquire and/or process any suitable image data from various sensors or imaging devices in communication with computing device 1200. For example, imaging subsystem 1210 can be configured to acquire OCT image data, e.g., interferograms, as part of an OCT system, e.g., OCT system 1102 described above. Imaging subsystem 1210 can be combined with logic subsystem 1202 and/or data-holding subsystem 1204 in a shared enclosure, or such imaging subsystems can comprise periphery imaging devices. Data received from the imaging subsystem can be held by data-holding subsystem 1204 and/or removable computer-readable storage media 1212, for example.

It is to be understood that the configurations and/or approaches described herein are exemplary in nature, and that these specific embodiments or examples are not to be considered in a limiting sense, because numerous variations are possible. The specific routines or methods described herein can represent one or more of any number of processing strategies. As such, various acts illustrated can be performed in the sequence illustrated, in other sequences, in parallel, or in some cases omitted. Likewise, the order of the above-described processes can be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A method of optical coherence tomography (OCT) angiography (OCTA), the method comprising:
    receiving an OCT dataset with complex values;
    performing phase stabilization on the OCT dataset to generate a phase-stabilized OCT dataset;
    performing a complex decorrelation on the phase-stabilized OCT dataset to generate an OCTA dataset, wherein the complex decorrelation is based on a phase difference between repeated scans of the phase-stabilized OCT dataset, and amplitude signals from the repeated scans; and
    generating one or more OCTA images based on the OCTA dataset.

2. The method of claim 1, wherein the complex decorrelation is performed according to:

$$PSCD = \sum_{n=1}^{N-1} \frac{[A_n(x, z) + A_{n+1}(x, z)]^2 \cdot \theta_n(x, z)}{A_n^2(x, z) + A_{n+1}^2(x, z)},$$

wherein PSCD corresponds to the OCTA dataset, $A_n$ and $A_{n+1}$ correspond to amplitude signals from two repeated scans of the phase-stabilized OCT dataset, and $\theta_n(x, z) = \varphi_n - \varphi_{n+1}$ corresponds to a phase difference between the two repeated scans of the phase-stabilized OCT dataset.

3. The method of claim 2, wherein the phase difference between the two repeated scans of the OCT dataset corresponds to:

$$\theta_n(x, z) = \left| a\tan \frac{imag(C_n(x, z) \cdot C_{n+1}(x, z)^*)}{real(C_n(x, z) \cdot C_{n+1}(x, z)^*)} \right|,$$

wherein $C_n$ and $C_{n+1}$ corresponds to a complex signal from the two repeated scans of the phase-stabilized OCT dataset, a tan is an inverse tangent, "imag" is an imaginary part of a complex variable, and "real" is a real part of the complex variable.

4. The method of claim 1, wherein the phase stabilization is performed using a standard-deviation-based bulk motion compensation method.

5. The method of claim 4, wherein the standard-deviation-based bulk motion compensation method is performed based on:

$$\Delta\phi_{B+M} = a\tan2\left(\frac{v_1 - v_3}{v_2 - v_0}\right).$$

wherein $\Delta\phi_{B+M}$ is a bulk-motion phase shift, a tan 2 is a four-quadrant inverse tangent, and $v_j$ is a variance.

6. The method of claim 5, wherein the variance is determined according to:

$$v_j = std\left(\left| C_n(x, z) - C_{n+1}(x, z) \cdot \exp\left(-i \cdot j \cdot \frac{\pi}{2}\right) \right|\right)^2.$$

wherein std(•) is a standard deviation, C is the complex signal, $v_j$ is indexed by j, and n is a scan index.

7. The method of claim 1, wherein performing the phase stabilization includes performing a bulk-motion compensation method and performing a trigger jitter compensation method.

8. The method of claim 1, wherein the OCTA dataset is a phase-based OCTA dataset.

9. The method of claim 1, wherein the OCTA dataset is a complex-based OCTA dataset.

10. A system for optical coherence tomography (OCT) angiography (OCTA), the system comprising:
    an OCT system to acquire an OCT dataset of a sample, wherein the OCT dataset includes complex values;
    a logic subsystem; and
    a data holding subsystem comprising machine-readable instructions stored thereon that are executable by the logic subsystem to:
    perform phase stabilization on the OCT dataset to generate a phase-stabilized OCT dataset;
    perform a complex decorrelation on the phase-stabilized OCT dataset to generate an OCTA dataset, wherein the complex decorrelation is based on a phase difference between repeated scans of the phase-stabilized OCT dataset, modified by amplitude signals from the repeated scans; and generate one or more OCTA images based on the OCTA dataset.

11. The system of claim 10, wherein the complex decorrelation is performed according to:

$$PSCD = \sum_{n=1}^{N-1} \frac{[A_n(x, z) + A_{n+1}(x, z)]^2 \cdot \theta_n(x, z)}{A_n^2(x, z) + A_{n+1}^2(x, z)},$$

wherein PSCD corresponds to the OCTA dataset, $A_n$ and $A_{n+1}$ correspond to amplitude signals from two repeated scans of the phase-stabilized OCT dataset, and $\theta_n(x, z) = \varphi_n - \varphi_{n+1}$ corresponds to a phase difference between the two repeated scans of the phase-stabilized OCT dataset.

12. The system of claim 11, wherein the phase difference between the two repeated scans of the OCT dataset corresponds to:

$$\theta_n(x, z) = \left| a\tan \frac{imag(C_n(x, z) \cdot C_{n+1}(x, z)^*)}{real(C_n(x, z) \cdot C_{n+1}(x, z)^*)} \right|,$$

wherein $C_n$ and $C_{n+1}$ corresponds to a complex signal from the two repeated scans of the phase-stabilized OCT dataset, a tan is an inverse tangent, "imag" is an imaginary part of a complex variable, and "real" is a real part of the complex variable.

13. The system of claim 10, wherein to perform the phase stabilization includes to perform standard-deviation-based bulk motion compensation.

14. The system of claim 13, wherein the standard-deviation-based bulk motion compensation is performed based on:

$$\Delta\phi_{B+M} = a\tan2\left(\frac{v_1 - v_3}{v_2 - v_0}\right).$$

wherein $\Delta\phi_{B+M}$ is a bulk-motion phase shift, a tan 2 is a four-quadrant inverse tangent, and $v_j$ is a variance.

15. The system of claim 14, wherein the variance is determined according to:

$$v_j = std\left(\left|C_n(x, z) - C_{n+1}(x, z) \cdot \exp\left(-i \cdot j \cdot \frac{\pi}{2}\right)\right|\right)^2.$$

wherein std(•) is a standard deviation, C is a complex signal, $v_j$ is indexed by j, and n is a scan index.

16. The system of claim 10, wherein to perform the phase stabilization includes to perform bulk-motion compensation and perform trigger jitter compensation.

17. The system of claim 10, wherein the OCTA dataset is a phase-based OCTA dataset.

18. The system of claim 10, wherein the OCTA dataset is a complex-based OCTA dataset.

19. The method of claim 1, wherein the phase stabilization uses a pixel-wise standard deviation of variance images constructed from repeated scans.

20. The method of claim 1, wherein the complex decorrelation normalizes the amplitude signals according to a tissue reflectance.

* * * * *